US00PP33604P2

(12) United States Plant Patent
Thiede

(10) Patent No.: US PP33,604 P2
(45) Date of Patent: Nov. 2, 2021

(54) ***DIANTHUS* PLANT NAMED 'KLEDP20383'**

(50) Latin Name: *Dianthus caryophyllus*
Varietal Denomination: KLEDP20383

(71) Applicant: Klemm+Sohn GmbH & Co. KG, Stuttgart (DE)

(72) Inventor: Lena Thiede, Bempflingen (DE)

(73) Assignee: KLEMM+SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 17/063,013

(22) Filed: Oct. 5, 2020

(51) Int. Cl.
*A01H 5/02* (2018.01)
*A01H 6/30* (2018.01)

(52) U.S. Cl.
USPC ..... Plt./272
CPC ..... *A01H 6/305* (2018.05)

(58) Field of Classification Search
USPC ..... Plt./272
CPC ..... A01H 6/305; A01H 5/02
See application file for complete search history.

*Primary Examiner* — Keith O. Robinson
(74) *Attorney, Agent, or Firm* — Weatherly IP Solutions, LLC; James M. Weatherly

(57) ABSTRACT

A new *Dianthus* plant designated 'KLEDP20383' particularly distinguished by red-purple flower color in winter, that changes to light pink then fading to almost white; and a pink flower color in summer with a light pink eye, is disclosed.

2 Drawing Sheets

Genus and species: *Dianthus caryophyllus*.
Variety denomination: 'KLEDP20383'.

BACKGROUND OF THE NEW PLANT

The present invention comprises a new and distinct variety of *Dianthus*, botanically known as *Dianthus caryophyllus* and hereinafter referred to by the variety name 'KLEDP20383'. 'KLEDP20383' is a selection that resulted from a controlled cross pollination of the commercial female *Dianthus* line 'KLEDP16188' (U.S. Plant Pat. No. 30,299) and the proprietary male *Dianthus* line 'DCP-2012-0206'.

In the summer of 2016, the female *Dianthus* line 'KLEDP16188' and the male *Dianthus* line 'DCP-2012-0206' were cross pollinated in Stuttgart, Germany and seeds were obtained. The seeds were sown and plants were grown for evaluation. A plant line was selected in May of 2017 in Stuttgart, Germany, and named 'KLEDP20383'. In May of 2017, 'KLEDP20383' was first vegetatively propagated by vegetative cuttings. 'KLEDP20383' was found to reproduce true to type in successive generations of asexual propagation via vegetative cuttings in Stuttgart, Germany and Latina, Italy.

SUMMARY

The following are the most outstanding and distinguishing characteristics of 'KLEDP20383' when grown under normal horticultural practices in Latina, Italy and Stuttgart, Germany.

1. Red-purple flower color in winter, that changes to light pink then fading to almost white; and
2. Pink flower color in summer with a light pink eye.

DESCRIPTION OF THE PHOTOGRAPHS

This new *Dianthus* plant is illustrated by the accompanying photographs. The colors shown are as true as can be reasonably obtained by conventional photographic procedures.

Figure 1:
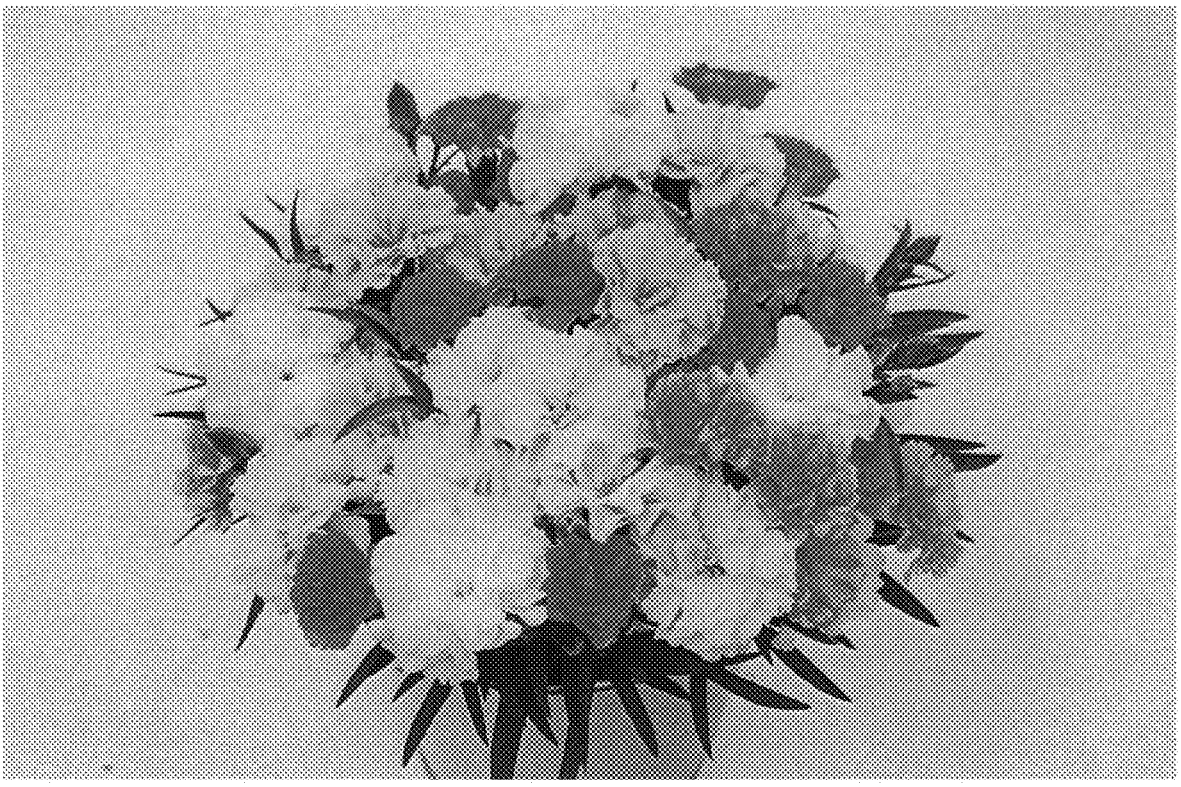
Figure 2:
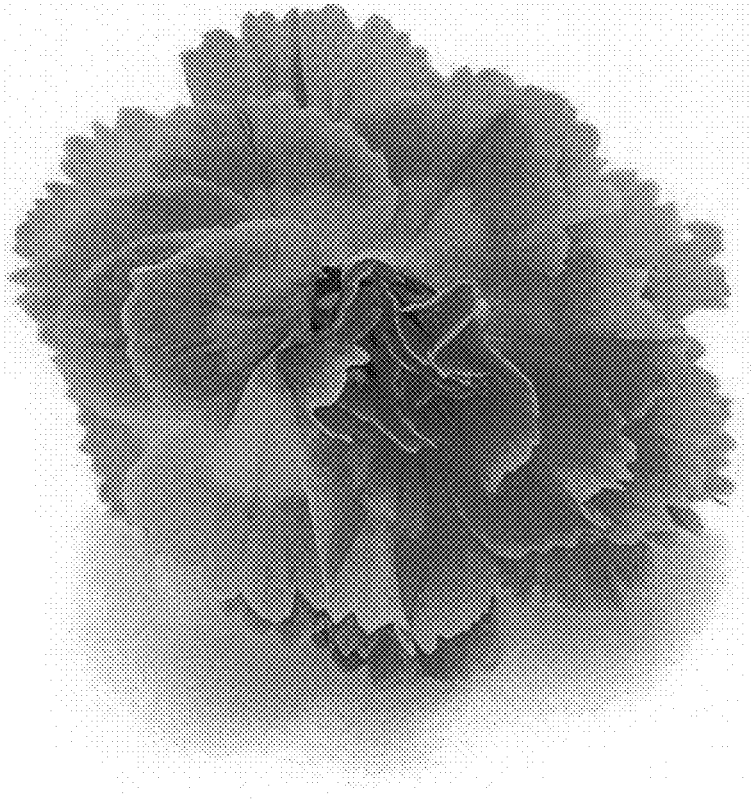

FIG. 1 shows the whole plant in winter, including the flowers and foliage and buds, taken in Stuttgart, Germany; and FIG. 2 show a close-up of a flower in summer, taken in Latina, Italy.

The photos are of 14-week-old plants of 'KLEDP20383'.

DESCRIPTION OF THE NEW VARIETY

The following detailed descriptions set forth the distinctive characteristics of 'KLEDP20383'. The data which define these characteristics were collected from asexual reproductions carried out in Stuttgart, Germany. Data for all characteristics was collected in July of 2020 on plants potted (indoor) and in week six of 2020. The flower color for summer production was measured on plants potted in week 10 (outdoor). Color references are to The R.H.S. Colour Chart of The Royal Horticultural Society of London (R.H.S.), 5$^{th}$ edition (2007).

Classification:
- *Family*.—Caryophyllaceae.
- *Botanical*.—*Dianthus caryophyllus*.
- *Common*.—Pot carnation.
- *Designation*.—'KLEDP20383'.

Parentage:
- *Female*.—'KLEDP16188' (U.S. Plant Pat. No. 30,299).
- *Male*.—The proprietary line 'DCP-2012-0206'.

Plant:
- *Propagation type*.—Vegetative cuttings.
- *Time to produce a rooted young plant*.—5 weeks.
- *Rooting description and habit*.—Fine, free branching white RHS 156C.
- *Rooting habit*.—Lanceolate.
- *Plant form*.—Upright.
- *Plant height*.—10.0 cm.
- *Plant diameter or spread*.—19.0 cm.

Lateral branches:
*Length.*—10.0 cm.
*Diameter.*—0.2 cm.
*Shape in cross section.*—Circular.
*Hollowness of stem.*—Absent.
*Number of internodes.*—3.
*Internode length.*—2.0 cm.
*Internode thickness.*—Thin.
*Node length.*—0.2 cm.
*Node diameter.*—0.4 cm.
*Texture.*—Smooth.
*Color.*—RHS 139B.

Foliage:
*Arrangement.*—Opposite.
*Length.*—6.9 cm.
*Width.*—0.6 cm.
*Shape.*—Linear.
*Apex.*—Acute.
*Base.*—Obtuse.
*Margin.*—Entire.
*Curvature.*—Very weekly curved.
*Glaucosity.*—Medium.
*Cross section of the leaf.*—Very weakly concave.
*Texture (both upper and lower surfaces).*—Smooth.
*Immature leaf color.*—Upper surface: RHS N137D. Lower surface: RHS N137C.
*Mature leaf color.*—Upper surface: RHS N137B. Lower surface: RHS N137B.
*Venation pattern.*—Parallel.
*Venation color (both upper and lower surfaces).*—RHS 138A.

Flowers:
*Flower type and habit.*—Round, wavy, small sprays with red-purple flower color, that changes to light pink then fading to almost white.
*Position of flowers compared to foliage.*—Same level.
*Fragrance.*—Sweet.
*Natural flowering season.*—Spring to fall.
*Flower longevity on the plant.*—10 to 15 days.
*Flower diameter.*—3.7 cm.
*Clustering of flowers on lateral branches.*—In some lateral branches.
*Buds.*—Length: 1.9 cm. Diameter: 0.8 cm. Shape: Oblong. Color: RHS 143A.
*Corolla.*—Quantity of petals per flower/arrangement: 18. Corolla height: 1.2 cm. Petal length: 2.2 cm. Petal width: 1.8 cm. Petal shape: Obtuse. Petal apex: Obtuse. Petal base: Acute. Petal margin: Crenate. Petal texture (both surfaces): Smooth. Profile of the upper and lower parts of corolla in lateral view: Flat convex. Petal color, immature and mature (Over winter/spring indoor) Upper surface: Red-purple (RHS N57C) flower color, that changes to light pink (RHS 62A) then fading to almost white (RHS 63D). Lower surface: RHS 61D. Petal color, immature and mature (Summer/outdoor) Upper surface: RHS 62A with a RHS 62D eye. Lower surface: RHS 61D.
*Calyx.*—Quantity of sepals per flower: 5. Calyx height: 1.6 cm. Calyx diameter (at the apex): 0.8 cm. Shape of the calyx: Straight. Longitudinal axis of the lobes of the calyx: Straight. Sepal texture (both upper and lower surfaces): Smooth. Sepal color: Upper surface: RHS 144A. Lower surface: RHS 145B.

Peduncles:
*Length.*—0.8 cm.
*Diameter.*—0.1 cm.
*Strength.*—Medium-strong.
*Texture.*—Smooth.
*Color.*—RHS 137B.

Reproductive organs:
*Stamens.*—Not present.
*Pistils.*—Quantity per flower: 2. Pistil length: 1.7 cm. Number of styles: 2. Description of the shoulder of the style: Absent. Style length: 0.1 cm. Style color: RHS 157A. Stigma shape: Filamentous. Stigma color: RHS 64C. Ovary size: 0.5 cm. Ovary shape: Obovate. Ovary texture: Smooth. Ovary color: RHS 145C.

Fruit and seed set: Seed information is not available.

Disease and pest/insect resistance: No disease and pest/insect resistance observed.

COMPARISON OF 'KLEDP20383' WITH PARENTAL LINES AND KNOWN VARIETY

'KLEDP20383' is distinguished from the parental lines as described in Table 1.

TABLE 1

Comparison with Parental Lines

| Trait | Variety 'KLEDP20383' | Female parent 'KLEDP16188' | Male Parent 'DCP-2012-0206' |
|---|---|---|---|
| Flower color | Red-purple flower color, that changes to light pink then fading to almost white in winter; pink with a light pink eye in summer | Lavender | Pink |

'KLEDP20383' can be compared to the commercial *Dianthus* variety 'KLEDP19309' (U.S. Plant Pat. No. 32,427). Differences between the varieties are described in Table 2.

TABLE 2

Comparison with Similar Variety

| Trait | Variety 'KLEDP20383' | Commercial line 'KLEDP19309' |
|---|---|---|
| Flower color | Red-purple flower color, that changes to light pink then fading to almost white in winter; pink with a light pink eye in summer | Purple |
| Bud color | Green | Brown |

I claim:

1. A new and distinct cultivar of *Dianthus* Plant Named 'KLEDP20383' as described and illustrated herein.

* * * * *